(12) United States Patent
Tamarkin

(10) Patent No.: US 6,180,669 B1
(45) Date of Patent: Jan. 30, 2001

(54) METHOD FOR TREATMENT OF DERMATOLOGICAL DISORDERS

(75) Inventor: Dov Tamarkin, Macabim (IL)

(73) Assignee: Tamarkin Pharmaceutical Innovation Ltd. (IL)

( * ) Notice: Under 35 U.S.C. 154(b), the term of this patent shall be extended for 0 days.

(21) Appl. No.: 09/286,236

(22) Filed: Apr. 5, 1999

Related U.S. Application Data

(63) Continuation-in-part of application No. PCT/IB97/01428, filed on Nov. 12, 1997.
(60) Provisional application No. 60/030,512, filed on Nov. 12, 1996.

(51) Int. Cl.$^7$ ................................................. A01N 37/00
(52) U.S. Cl. ..................... 514/548; 514/532; 514/533; 514/557; 514/558; 514/559; 514/844; 514/859; 514/863; 514/864; 514/880; 554/229
(58) Field of Search ............................... 514/532, 533, 514/548, 557, 558, 559, 844, 859, 863, 864, 880; 554/229

(56) References Cited

U.S. PATENT DOCUMENTS

| | | |
|---|---|---|
| 1,979,559 | 11/1934 | Kyrides . |
| 3,462,468 | 8/1969 | Taylor et al. . |
| 3,660,467 | 5/1972 | Gould et al. . |
| 4,034,077 | 7/1977 | Hill et al. . |
| 4,292,326 | 9/1981 | Nazzaro-Porro . |

(List continued on next page.)

FOREIGN PATENT DOCUMENTS

| | | |
|---|---|---|
| 42 13 419 A1 | 10/1993 | (DE) . |
| 0 336 880 A2 | 10/1989 | (EP) . |
| 0 297 436 B1 | 4/1995 | (EP) . |
| 0 588 379 B1 | 8/1996 | (EP) . |
| 2616430 | 12/1988 | (FR) . |
| 1 603 620 | 11/1981 | (GB) . |
| 2 285 805 | 7/1995 | (GB) . |
| 761452 | 9/1980 | (RU) . |

OTHER PUBLICATIONS

Müller et al. "4–Hydroxycoumarins. II. 4–Hydroxy–3–coumarinpropionic acid and 4–hydroxy–3–coumarinbutyric acid" Chemical Abstracts vol. 44, No. 18, column 8352h, (Sep. 25, 1950) Abstract only.

(List continued on next page.)

*Primary Examiner*—Deborah D. Carr
(74) *Attorney, Agent, or Firm*—Clark & Elbing LLP; Mary Rose Scozzafava

(57) ABSTRACT

A compound effect for the treatment of dermatological disorders comprises a mono- or diester of an α,ω-dicarboxylic acid, wherein the alcohol moiety of the said ester comprises a keratolytically active alcohol. The compound may have the formula,

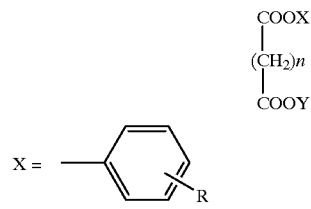

where n is in the range of 6 to 12; m is in the range of 0 to 8; R' is selected from the group consisting of H, alkyl, aryl, alkenyl, benzyl, OH, NHR", CONHR" and COOR"; R" is selected from the group consisting of alkyl, aryl, alkenyl, and benzyl; and Y is selected from the group consisting of H, alkyl, aryl, alkenyl, benzyl and X.

48 Claims, 1 Drawing Sheet

U.S. PATENT DOCUMENTS

| | | |
|---|---|---|
| 4,299,826 | 11/1981 | Luedders . |
| 4,386,104 | 5/1983 | Nazzaro-Porro . |
| 4,818,768 | 4/1989 | Nazzaro-Porro . |
| 4,885,282 | 12/1989 | Thornfeldt . |
| 5,326,790 | 7/1994 | Thornfeldt . |
| 5,387,672 | 2/1995 | Bucci et al. . |
| 5,494,924 | 2/1996 | Cavazza et al. . |
| 5,547,989 | 8/1996 | Chamness . |

OTHER PUBLICATIONS

Chemical Abstract 119:278 796w "Topical pharmaceutical preparation containing glycerol nitrate as penetration enhancer," (DE 4,213,419); vol. 119(26) Dec. (1993).

Bilibin et al., "Thermotropic polyesters, 1 Synthesis of complex monomers for polycondensations," *Makromol. Chem., Rapid Commun.* 6:209–213 (1985) (abstract).

Portnoy et al., "Esters of aromatic alcohols and dibasic acids as base stocks for nonspreading oil compositions," *Chemical and Engineering Data Series* 3(2):287–293 (1958).

Sugibayashi et al., "Effect of several penetration enhancers on the percutaneous absorption of indomethacin in hairless rats," *Chem. Pharm. Bull.* 36(4):1519–1528 (1988).

METHOD FOR TREATMENT OF DERMATOLOGICAL DISORDERS

CROSS REFERENCE TO RELATED APPLICATIONS

This application is a continuation-in-part application of International Application No. PCT/IB97/01428, filed Nov. 12, 1997 and entitled "Method for Treatment of Dermatological Disorders", and which designates the United States, which is a continuation-in-part application of U.S. Ser. No. 60/030,512, filed Nov. 12, 1996 and entitled "Method for Treatment of Dermatological Disorders", which are incorporated in their entireties by reference.

FIELD OF THE INVENTION

The invention relates to active agents, cosmetic or pharmaceutical compositions, and the administration of such compositions in order to treat mammalian dermatological disorders.

BACKGROUND OF THE INVENTION

Numerous skin disorders result in the hypertrophy of the stratum corneum, an occurrence also described as hyperkeratinization. The thickened superficial layer of the epidermis results in scale-like plaques on the surface of the skin. These scaly plaques are the manifestation of a group of disorders termed ichthyoses because of their resemblance to fish scales. The plaques may be symptoms of a skin disorder and accordingly prohibit the treatment of these disorders originating in underlying layers of the skin. The hypertrophied skin layer may also harbor infections within itself.

Typical examples of ichthyoses which do not have known etiologies include psoriasis, pityriases, rosacea, and seborrheic dermatitis. These disorders are treated symptomatically with keratolytic agents to remove the plaques and with glucocorticoids to alleviate inflammation. Dermaphytoses are ichthyoses caused by fungal infections. The hyphae and spores are confined to nonviable portions of tissue and thus proliferate in the hyperkeratinized tissues of skin, hair, and nails. Examples of typical dermaphytoses include tinea capitis (cradle cap), tinea pedis (athlete's foot), and tinea unguium. These disorders are treated with anti-fungal agents, and topically with keratolytic agents to remove the cornified and infected layer.

Skin disorders may also be caused by a hormonal imbalance. Such an imbalance may cause increased levels of testosterone, as in the onset of puberty. Testosterone is reduced to dihydrotestosterone (DHT) in target tissues, including the sebaceous glands. In the common dermatological disorder acne, DHT binds to receptors in the pilosebaceous complex and stimulates excessive sebum secretion. The sebum acts as a nutrient for bacteria such as *Propionibacterium acnes*, which infect the sebaceous gland and lead to an inflammatory response and abnormal cornification of the skin. Acne is typically treated with antibacterial and antiseptic agents, and also with keratolytic agents, such as salicylic acid or retinoic acid, to remove the hyperkeratinized tissue.

The terms eczema and dermatitis are generally used names for severe inflammation of the skin, usually with redness, swelling, oozing, rusting or scaling of lesions which are usually itchy. Eczema may take the form of contact dermatitis (due to skin contact with the cause) or atopic dermatitis in individuals who are "atopic" or allergic by nature. If the scalp is involved the disorder is known as seborrheic dermatitis. Dermatitis can be caused by chemicals, plants, shoes, clothing, metal compounds and even medicines used to treat dermatitis. In atopic dermatitis environmental temperature, humidity changes, bacterial skin infections, airborne allergens and garments, e.g., wool, may all bring about dermatitis.

Alopecia areata is a common condition that results in the loss of hair on the scalp and elsewhere. It usually starts with one or more small, round, smooth patches and occurs in males and females of all ages, but young persons are affected most often. Most patients just lose one spot of hair, or two to three small spots, but it is possible to lose all scalp hair (alopecia totalis), or, even more rarely, every hair on the body (alopecia universalis). Modern immunological research is showing that alopecia areata is probably an autoimmune disorder, one in which the body forms antibodies against some part of the hair follicle (a type of "self-allergy").

Skin disorders, such as those described above, create aesthetic disturbances, treatment of which sometimes are regarded as cosmetic processes. They may be treated using known medications, however, it is common knowledge that cosmetic products, e.g., soaps, lotions, and shampoos, also include ingredient to combat conditions such as acne, dandruff, seborrhea and androgenic alopecia.

Azelaic acid (AZA) is a naturally occurring nine carbon straight chain molecule with two terminal carboxyl groups. AZA is an anti-keratinizing agent, displaying antiproliferative effects on keratinocytes and modulating the early and terminal phases of epidermal differentiation (Passi, et al. *G. Ital. Dermatol. Venerol.* 1989, 124(10):455–463). AZA is a competitive inhibitor of the reduction of testosterone to dihydrotestosterone, and as such is supposed to reduce the production of sebum in the sebaceous gland. Furthermore, recent investigations have demonstrated that AZA and sebacic acid also have anti-bacterial and anti-fingal properties. Structure-activity relationship studies have revealed that these effects are retained when the $\alpha,\omega$-dicarboxylic acid has a backbone of about 6 to about 14 carbons.

Thus, azelaic acid, and other $\alpha,\omega$-dicarboxylic acids, may be used as therapeutic agents in the treatment of skin disorders; however, treatment of the above disorders is hindered by the low bioavailability of such therapeutic agents. Dicarboxylic acids such as azelaic acid are very polar due to the two carboxyl groups. Because of this polarity, skin penetration is very low. In addition, the presence of the acid functional group lowers the pH, which may cause irritation of the skin. Only high concentrations of the azelaic acid in topical preparations (20%) are effective in treating acne. To demonstrate how weak is the therapeutic effect of AZA lotion, a 20% preparation was effective only after 3–6 months of topical application, twice daily. See, A. Fitton and K. L. Goa, *Drugs* 41: 780–798 (1991). Furthermore, in additional studies topical administration of AZA failed to induce specific changes in sebum composition, sebum excretion rate and the size of sebaceous glands (See for example Mayer-da-Silva et al, 1989, *Acta Derm. Venereol. Suppl.* (Stockholm) 143: 20–30). Other dermatological agents also comprise a polar functional group, such as a carboxy or hydroxy group, rendering their skin penetration relatively low. Thus there remains a need to increase the efficacy of these drugs in the treatment of skin disorders in which the availability of the drugs through topical application is improved.

$\alpha,\omega$-Dicarboxylic acids, and their mercapto, ester and salt derivatives have been used in the treatment of a variety of skin disorders and/or conditions. Relevant discussions on their uses may be found in the following references.

Hill et al in U.S. Pat. No. 4,034,077 teaches the use of a composition comprising sebacic acid for the treatment of skin irritation and the prevention of diaper rash in which the dicarboxylic acid acts as a barrier between the urine and the skin and also neutralizes ammonia. It does not teach the use of sebacic acid in the treatment of any endogenous disorder, including any form of ichthyosis, or any hormonal imbalance.

Nazzaro-Porro (U.S. Pat. No. 4,292,326) discloses a method of treating hyperpigmentary dermatoses with dicarboxylic acids, such as azelaic acid. These acids, along with their mono- and dimercapto derivatives, are used for their ability to normalize skin color by inhibiting melanogenesis. Nazzaro-Porro (U.S. Pat. No. 4,386,104) teaches the use of the same compounds for the treatment of acne. It also teaches adding a small amount of keratolytic agent to the composition. Nazzaro-Porro (U.S. Pat. No. 5,385,943) also discloses the use of topically applied preparations, comprising an ester of a dicarboxylic acid cleavable by skin enzymes, particularly a glycerol ester, for treatment of presbyderma of the aging skin.

Thornfeldt (U.S. Pat. No. 4,885,282) discloses a treatment of hyperhydrosis, ichthyosis and wrinkling of the skin by means of a mono- or di-carboxylic acids (4–18C), along with their mercapto derivatives, salts and esters. The use of alkyl, polyol, oligosaccharide and polysaccharide esters, and specifically glycerol, polyethylene glycol, polypropylene glycol and sucrose esters of the respective mono- or di-carboxylic acids is described. UK Pat. Appl. No. GB 2,285,805 teaches the use of esters of dicarboxylic acids with vitamins A, E and D as antitumor agents. Chamness (U.S. Pat. No. 5,547,989) teaches a topical composition comprising dicarboxylic acids (7–13C and specifically AZA), salts and esters thereof for treating corns and calluses. However, no specific ester is claimed or demonstrated by an example.

Sugibayashi et al (Chem. Pharm. Bull., 36(4): 1519–1528 (1988)) teaches the use of penetration enhancers for the model compound indomethacin. It discloses the use of salicylates as enhancers because of their ability to soften and dissolve the stratum corneum. They teach the use of salicylates as keratolytic agents to remove the outer layer of cells, which then allows easier penetration of the desired compound.

Luedders, (U.S. Pat. No. 4,299,826) teaches a physical mixture of the antibacterial agent erythromycin, with the penetration enhancer diisopropyl sebacate. Luedders teaches that this additive increases the penetration of erythromycin. DE 4213419 discloses a salicylic acid ester derivative of azelaic acid in a glycerin trinitrate carrier for pharmaceutical applications. The low pH of the salicylic acid ester tends to irritate the treated tissues.

Known references disclose complex esters of straight chain dicarboxylic acids. In U.S. Pat. No. 5,494,924, Cavazza et al. teaches the treatment of ichthyoses using complex esters of α,ω-dicarboxylic acids and carnitine. Bilibin et al. (USSR Pat. No. 761,452) teaches the synthesis of straight carbon chain α,ω-dicarboxylic acids esterified by reaction with p-hydroxy benzoates, which are used as monomers for the formation of liquid crystalline polymers. In U.S. Pat. No. 3,660,467, Gould teaches phenoxy phenyl esters of α,ω-dicarboxylic acids for use as synthetic lubricants and heat transfer fluids. Portnoy et al (Chemical Engineering Data Series, 1958, 3: 287–293) teaches the use of phenyl α,ω-dicarboxylates in the development of nonspreading lubricant oils. Although the aforementioned an describes compounds comprising esterified α,ω-dicarboxylic acids, there is no discussion of the use of these compounds in treatment of skin disorders.

Thus, there remains a need to provide therapeutic agents for the treatment of skin disorders which demonstrate improved efficacy and reduced irritation over the agents available in the prior art.

SUMMARY OF THE INVENTION

One aspect of the invention provides novel compounds comprising of ester derivatives of α,ω-dicarboxylic acids effective in treating skin disorders and in improving the appearance of the skin.

Another aspect of the invention includes cosmetic or pharmaceutical compositions comprising such novel ester derivatives for the treatment of skin disorders and improvement of skin appearance.

Advantageously, these novel compositions are capable of increased penetration across the skin.

In addition, the novel compositions are able to treat multiple aspects of a skin disorder.

Another aspect of the present invention is a novel dual-action pro-drug capable of delivering multiple therapeutically active agents to a skin site of a patient.

Yet a further aspect of the invention includes therapeutic treatments effective in mitigating the symptoms of hyperkeratinization, excessive sebum secretion, microbial infection, dermaphytoses, and excessive conversion of testosterone to dihydrotestosterone.

And yet a further aspect of the invention includes therapeutic treatments effective in mitigating the symptoms of acne, psoriasis, seborrheic dermatitis, ichthyosis, Rosacea, dandruff, hirsutism, hypertrichosis, and androgenic alopecia.

In one aspect of the present invention, novel ester derivatives of α,ω-dicarboxylic acids are provided. The compound includes an α,ω-dicarboxylic acid moiety covalently linked, e.g., esterified, with at least one keratolytically active alcohol moiety. The compound may have the formula,

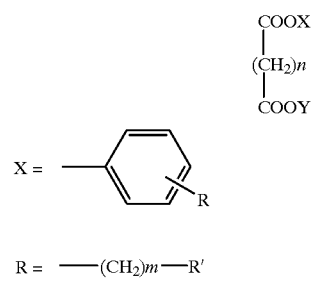

where n is in the range of 6 to 12; m is in the range of 0 to 8; R' is H, alkyl, aryl, alkenyl, benzyl, OH, NHR", COOR" or CONHR"; R" is H, alkyl, aryl alkenyl or benzyl; and Y is either H, alkyl, aryl, alkenyl, benzyl or X.

The compounds of the invention are useful in the pharmaceutical treatment for mitigation the symptoms of hyperkeratinization, excessive sebum secretion, microbial infection, dermaphytoses, and excessive conversion of testosterone to dihydrotestosterone or in mitigating the symptoms of acne, psoriasis, seborrheic dermatitis, ichthyosis, Rosacea, dandruff, hirsutism, hypertrichosis, androgenic alopecia, allergic and autoimmune dermatoses and hair growth abnormalities such as alopecia areata, alopecia universalis and alopecia totalis.

The compounds of the invention also are useful in cosmetic treatments and compositins used by non-medical specialists, i.e., lay persons, for combating conditions such as acne, dandruff, seborrhea and androgenic alopecia.

BRIEF DESCRIPTION OF THE DRAWING

The invention is described with reference to the figures which are presented for the purpose of illustration only and which are in no way limiting of the invention and in which.

DETAILED DESCRIPTION OF THE INVENTION

Figure 1:
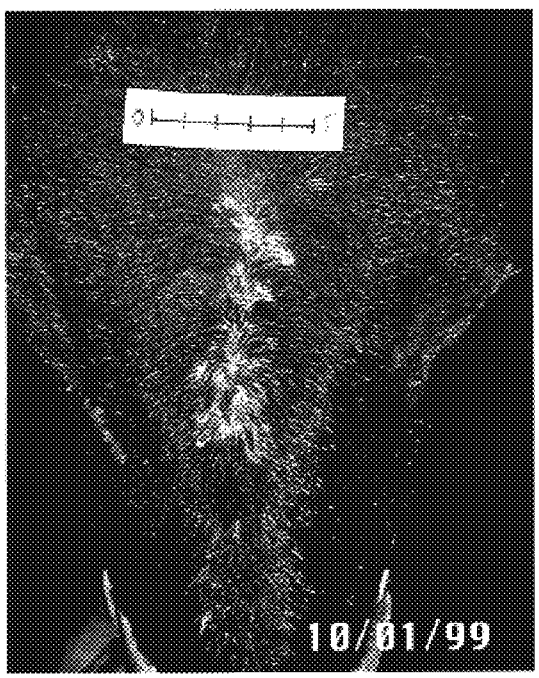
FIG. 1 is a photograph of the mane area of a horse afflicted with culicoides hypersensitivity.

The present invention provides novel compounds effective in the treatment of skin disorders. Such compounds can either be incorporated into pharmaceutical products to be prescribed by medical professional or in cosmetic preparations offered directly to customers for self usage.

According to the invention, the compounds include an $\alpha,\omega$-dicarboxylic acid moiety which is covalently linked through an ester bond to a keratolytically active alcohol. The compound may contain one or two alcohols to provide either the respective mono- or diester. As such, the compound comprises two moieties, an $\alpha,\omega$-dicarboxylic acid and a keratolytic agent, each capable of treating the symptoms of a variety of skin disorders or to improve the appearance of the skin. The compound possesses the additional advantage of providing the two moieties in a form which penetrates rapidly into a dermal site.

An "$\alpha,\omega$-dicarboxylic acid moiety" is used herein to mean a straight carbon chain terminating on both ends with a carboxylic acid functional group. The length of the $\alpha,\omega$-dicarboxylic acid moiety is about 6 to 14 carbons. In a preferred embodiment, the $\alpha,\omega$-dicarboxylic acid moiety comprises between 8 and 10 carbons. The carbon chain backbone may be saturated or unsaturated. In preferred embodiments, the unsaturated backbone may contain 1–3 double bonds. The straight carbon chain also may be substituted, for example, it may be linked to hydrocarbon groups along the carbon atom backbone. Suitable $\alpha,\omega$-dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. In a preferred embodiment, the $\alpha,\omega$-dicarboxylic acid is azelaic acid. Suitable substitutions along the carbon chain backbone include, but are not limited to, alkyl, aryl, alkenyl, and benzyl groups. By way of example only, suitable hydrocabons, e.g., aryl and alkyl substituents, include methyl, ethyl, propyl, phenyl, benzyl and the like.

A "keratolytically active alcohol moiety" is used herein to mean a compound which loosens and removes the stratum corneum of the skin or having an antikeratinizing effect via modulation of keratinocyte differentiation and growth. Suitable keratolytic agent moieties include phenol and substituted phenolic compounds. Suitable substituents include but are not limited to hydroxy groups, —$(CH_2)_m$—COOH and —$(CH_2)_m$—COOR', where m=0–8 and R' is an aryl, alkyl, alkenyl and benzyl. By way of example only, suitable aryl and alkyl substituents include methyl, ethyl, propyl, phenyl, benzyl and the like. R' and R" are generally selected to impart hydrophobicity to the compound or to improve targeting of the compound to the site of action in order to improve skin penetration. The substituents on the phenyl ring additionally may impart therapeutic properties to the keratolytic phenol. For example, additional hydroxy groups may increase keratolytic performance, and presence of carboxylic acid or alkyl carboxylate substituents may impart anti-inflammatory properties. Other substituents may increase the hydrophobicity of the moiety. Keratolytic agents include, but are not limited to, $\alpha$-hydroxy acids and derivatives thereof, hydroxybenzoic acid and their ester, anhydride and amine derivatives, alkylhydroxybenzoate, dihydroxy benzene and their ester, anhydride and amide derivatives, cresols and their ester, anhydride and amide derivatives. Keratolytic agents also include alcohol derivatives of Vitamin A (retinoic acid), e.g., retinol and derivatives thereof.

Suitable keratolytic agents are effective for the treatment of various skin disorders. Salicylic acid (o-hydroxybenzoic acid) and its ester derivatives have anti-inflammatory, as well as keratolytic, activity. They are known to dissolve and loosen the intracellular matrix of the hyperkeratinized tissue. As such, they are used in the treatment of dermatological disorders. Dihydroxy benzene and derivatives thereof have been recognized as potent keratolytic agents. Resorcinol (m-dihydroxybenzene) and derivatives thereof are used in anti-acne preparations.

Hydroquinone (p-dihydroxybenzene), besides its anti-pigmentation properties, is also keratolytic. These compounds also exhibit antiseptic properties. Cresols also possess bactericidal and keratolytic properties. All of these compounds, when used alone, have limited pharmaceutical use because of their poor skin penetration and relatively weak potency. However, when covalently linked to an $\alpha,\omega$-dicarboxylic acid moiety according to the invention, these compounds experience increased skin penetration, and/or increased delivery to the affected site. Thus, the potency of these agents is increased significantly over those of the prior art.

A particularly preferred keratolytic agent is o-hydroxybenzoic acid. In other preferred embodiments, it may be desirable to use an alkyl o-hydroxybenzoates or an aryl o-hydroxybenzoates as the keratolytic alcohols. By way of example only, suitable aryl and alkyl substituents include methyl, ethyl, propyl, phenyl, benzyl and the like. Alkyl and aryl hydroxybenzoates have the added benefit of increased hydrophobicity over the acid counterpart, which increases the skin penetration. Further, aryl and alkyl hydroxybenzoate derivatives of $\alpha,\omega$-dicarboxylic acids form low melting point solids which are liquid at physiological temperatures. This property is useful in enhancing skin penetration.

The particularly preferred compound of the present invention has the general formula,

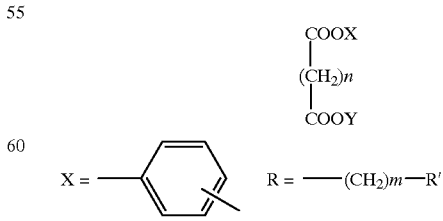

where n is 6–12; R is OH, COOH and COOR'; and R' may be alkyl, aryl, alkenyl, or benzyl. Y is either H, alkyl, aryl, alkenyl, benzyl or X. Most preferred is a compound where n=7; R is ortho-COOR'; and R' is an alkyl group. By way of example only, suitable aryl and alkyl substituents include methyl, ethyl, propyl, phenyl, benzyl and the like.

The chemical combination of the α,ω-dicarboxylic acid moieties with the aforementioned alcohols results in compounds having enhanced therapeutic effects for the treatment of skin disorders. Some embodiments have melting points around 30–40° C. These compounds are liquids at physiological temperatures, which increases the ease of skin penetration as compared to compounds which are solids at physiological temperatures.

Skin penetration is directly correlated with hydrophobicity. In the present invention, the polarity of carboxylic acid and hydroxy functional groups is masked by the reaction with one another to form a complex monoester or diester. As a complex ester, the novel derivatives of the present invention are more hydrophobic than the corresponding free α,ω-dicarboxylic acids and free alcohols, and this allows for increased penetration across the skin. With increased penetration, the compound may then exert its therapeutic effects in the underlying layers of the skin. These effects include, but are not limited to, the aforementioned properties of α,ω-dicarboxylic acid moieties, the keratolytic properties and the anti-inflammatory effects of specific alcohols thereof.

The compounds of the present invention may function as dual-action "pro-drugs", i.e., compounds that once delivered to the target site, undergo a chemical or enzymatic cleavage to produce the active form of the two corresponding active agents, namely the α,ω-dicarboxylic acid and the alcohol moiety, in their pharmacologically active forms. The skin naturally contains non-specific esterases which can effect the necessary cleavage. See, Montagna, W. *The Structure and Function of Skin,* 1962 2nd edition; and Stevens, C. S. and C-Villez, R. L. *Int. J. Dermatol.* 19:295 (1980). In particular, high concentrations of the nonspecific esterases are located inside the targeted sebaceous glands. See, Holt, R. J. *Br. J. Dermatol.* 85:18 (197). After penetration across the outer layers of the skin, the compounds of the present invention, interact with these esterases. Since the enzymes are not specific, they hydrolyze the ester bond linking the α,ω-dicarboxylic acid moiety and the alcohol moiety. Consequently, two therapeutically effective agents are released in their pharmacologically active forms.

The hydrophobicity of the pro-drug allows the penetration through the naturally occurring outer layers of the skin, as well as through abnormal plaques of hyperkeratinized cells. These plaques are often symptoms of the targeted disorder and barriers to the affected area. The hydrolysis reaction thus occurs in the underlying layers of the skin. The two pharmacologically active agents, capable of treating two or more separate symptoms of a disorder, bypass these barriers to reach the targeted tissue. There, they may then exert their respective therapeutic properties. Thus, it is possible to deliver two therapeutic agents to a target site using the novel compound of the invention.

The increased penetration of the present invention, and thus the improved delivery of the pharmacologically active agents to the targeted tissue, allows for more effective treatment of skin disorders than is known in the prior art. Because the efficiency of delivery is improved, amounts of active ingredients less than is previously disclosed in the prior art will alleviate a skin disorder. In addition, because the acidity of the agent is reduced by esterification, there is reduced inflammation and irritation at the site of application.

Another aspect of the invention is a pharmaceutical or cosmetic composition capable of treating two aspects of a skin disorder. The α,ω-dicarboxylic acid can exert its therapeutic effects on sebum secretion, keratinization of the skin, microbial and fungal infections with concomitant keratolysis of the stratum corneum and/or anti-inflammatory effect, exerted by the phenolic moiety.

In one embodiment of the invention, a composition comprising 10% by weight (200 mmole/ml) di(ethyl salicylate) azelate was effective in the reduction of comedones in a rabbit ear model. The comedolytic effect of the di(ethyl salicylate)azelate was comparable to the effect of 0.025% Retin A Cream. This comedolytic effect is superior to a 20% (1,060 mmole/ml) azelaic acid preparation disclosed in the prior art. See, Lee, et al. *Kor. J. Dermatol.* 28(5):543–549 (1990).

Additionally, treatment with this composition did not induce any inflammatory response in the treated area, as opposed to the inflammatory effect observed when treated with 0.025% Retin A. Moreover, a comparative skin-irritation test in human volunteers has demonstrated that di(ethyl salicylate)azelate (20%, 400 mmole/ml) did not irritate the skin. In contrast, an equimolar mixture of its components (7.5%, 400 mmole/ml azelaic acid and 11%, 800 mmole/ml salicylic acid) induced an inflammatory reaction, including moderate erythema, slight edema, and local pruritus. An in-vivo dermal irritation test in rabbits also demonstrated no signs of irritation following 24 hour application of di(ethyl salicylate)azelate (10% and 20%). These findings emphasize a distinct advantage of di(ethyl salicylate)azelate over its parent components.

The sebolytic effect of di(ethyl salicylate)azelate was revealed in a human test. Following fourteen days of topical treatment, the skin oiliness of the forehead of a human volunteer, tested using a photometric instrument was reduced from 223 units (resembling "oily skin") to 205 units (normal skin value). This finding demonstrates the superiority of the compounds of the invention over azelaic acid, which according to published literature can not alter skin oiliness.

The compounds of the present invention have been shown in animals to alleviate the symptoms of acne. Four cats with persistant chin acne were treated twice daily for 14 days with 5% alcoholic solution of di(ethyl salicylate) azelate. Three of the four cats responded to treatment within ten days. The skin lesions disappeared and the bald areas were covered with new hair. In a separate case, a cat suffering from furunculosis (eczema) was successfully treated using the same method of treatment.

The direct effect of the compounds of the invention on the proliferation of human keratinocytes was assessed in vitro using a keratinocyte cell line. It was found that compounds of the invention are strong inhibitors of keratinocyte proliferation. Di(ethyl salicylate)azelate inhibited cell proliferation at a concentration of 0.3 mM and di-retinyl azelate was inhibitory at a concentration of 15 $\mu$M. The cytotoxic respective concentrations of the same agents were 3 $\mu$M and 100 $\mu$M, allowing a substantial therapeutic safety margin of 6.6–10. In contrast, the inhibitory concentration of azelaic acid was as high as 1 mM and its cytotoxic concentration was only 2.6 times higher. Hence, utilizing the compounds of the invention in treatment of skin disorders that involve hyperkeratinization is advantageous over using free azelaic acid.

A preferred embodiment is a pharmaceutical or cosmetic composition comprising a therapeutically effective amount of the novel compound described herein and a pharmaceutically or cosmetically acceptable carrier. With respect to a "pharmaceutically acceptable carrier", as used herein, it is meant any liquid, gel, emulsion, cream, ointment, fluid ointment base, solvent, diluent and the like which is suitable for use in contact with living mammalian tissue, which is desirably capable of dissolving the therapeutically active agents of the invention, and which will not interact with the other components of the composition in a deleterious manner. Alcohols are particularly preferred carriers. Additives to such compositions may include, but are not limited to, preservatives, moisturizers, petroleum, thickening agents, alpha-hydroxy carboxylic acids, mineral oil, pigments and other components described in the CTFA handbook of cosmetic ingredients. It would be apparent to those of ordinary skill in the art of dermatology that the resulting compositions can be in many forms including, but not limited to, solutions, lotions, creams, pastes, emulsions, gels, soap bars, sprays or aerosols. Such compositions may be applied manually, or using various application devices.

Another aspect of the invention is a method of treating a particular skin disorder by applying a composition comprising an effective amount of the compound mixed with a pharmaceutically or cosmetically acceptable carrier to the affected area. The composition contains a therapeutically effective amount of the novel mono- or diester of the invention. The actual effective amount may vary dependent upon the particular skin disorder treated; however, it is generally contemplated that composition having 0.1%–30% (weight per volume) may be used in accordance with the invention. The composition may be applied topically to the affected area. By "topical" application as that term is used herein it is meant directly spreading or laying on the epidermal tissue. The application may be made by rubbing, by using medicated pads or by any other convenient means. Due to the very low toxicity of the compound of the invention, oral, nasal or parenteral administration of the agent is also applicable.

One aspect of the invention is a pharmaceutical or cosmetic composition and method for the treatment of hyperkeratinization. Another aspect of the invention is an effective composition and method of treating dermatological disorders resulting from a hormonal imbalance in target tissues. It has been suggested that α,ω-dicarboxylic acids inhibit the reduction of testosterone to dihydrotestosterone (DHT). By inhibiting this conversion, α,ω-dicarboxylic acids act as therapeutic agents in the treatment of disorders cause by an increase in the amount of dihydrotestosterone. DHT is the androgen responsible for the development of secondary sex characteristics. Increased levels of DHT may cause excessive hair growth, a disorder known as hypertrichosis. Both males and females may be afflicted by hypertrichosis in which there is increased hair growth on any part of the body. Another disorder which strikes females and is caused by increased levels of DHT is hirsutism. In this disorder, the increased levels of androgens cause the subject to develop male hair growth patterns. Since the aforementioned disorders are caused by an increased level of DHT at the hair follicle, they are frequently accompanied by an increased occurrence of acne. The increased penetration of the composition of the invention provides a method of delivering α,ω-dicarboxylic acid moieties to the underlying layers of the skin. Thus, the composition of the invention is expected to be effective in the treatment of secondary effects of hormonal imbalance.

Androgenic alopecia, also termed male pattern baldness, is a predominantly hereditary disease which is the most common cause of hair loss in men. The hair follicles have an increased sensitivity to DHT and to its subsequent breakdown products, which are thought to inhibit hair growth in the scalp. Thus, an increase in the amount of DHT at the hair follicle would increase this inhibition and lead to hair loss. Androgenic alopecia may also afflict women. Increased levels of circulating androgens in women may be caused by endocrine disorders, such as ovarian or adrenal dysfunction. In these women the excessive amounts of the androgen in the target tissue, specifically the hair follicles, inhibits hair growth and ultimately results in hair loss. The composition of the invention is expected to effectively reduce the amount of DHT at the hair follicles. This reduction will decrease the inhibition and promote hair growth.

Another aspect of the invention is a pharmaceutical composition and method of treatment for allergic dermatoses. Allergic dermatoses includes disorders such as eczema and dermatitis that result from contact with an allergen or atopic dermatitis. The α,ω-esters of the invention have been shown effective in the treatment of skin disorders caused by inflammatory factors, allergies and infections.

Canine flea allergy dermatitis (FAD) is one such example. FAD begins with the bite of a flea. It is manifested by scratching, chewing, licking, biting, and other signs of pruritus. Dogs usually have papules, crusts, salivary stains, excoriations, and erythema in a wedge-shaped pattern over the lumbosacral region, caudal thighs, proximal tail, ventral abdomen, and around the umbilicus. With chronic itching the areas become alopecic, lichenified, and hyperpigmented and the dog develops an odor related to secondary infections with *Staphylococcus internedius* and *Malassezia pachydermatis*.

Horses also suffer from allergic and inflammatory skin disorders. One cause of such disorders is insect bite irritation, particularly caused by culicoides. Culicoides hypersensitivity, also called 'Summer Eczema', 'Queensland Itch', 'Summer Seasonal Recurrent Dermatitis' and 'Sweet Itch' is a recurring warm season itching that worsens each year without treatment. Culicoides is a small biting midge that prefers the head, tail head, mane and ventral midline of the horse. The bite itself is irritating but some horses develop sensitivity to the bite and become very itchy and rub to the point of self-mutilation. The resulting skin disease is characterized by a localized dermatitis affecting the mane and poll and the root of the tail. In severe cases the shoulder area and hind quarters may be affected. Early in the development of the disease the skin becomes very thickened and filled with fluid and the intense irritation causes the horse to rub on any convenient post. At this stage a close look at the lesions will show many pustules with small blobs of serum oozing out on to the surface. As the itch becomes worse and the rubbing constant, the hair is gradually lost and the skin develops a corrugated appearance, becoming ridged and scaly. The mane may be lost completely and the tail may consist of a few scraggy hairs. In many respects, there may be similarities between the mentioned above veterinary conditions and human disorders such as atopic and allergic dermatitis, as well as immunologically-related hair growth disorders, e.g., alopecia areata, alopecia totalis and alopecia universalis.

Figure 2:
FIG. 2 is a photograph of the horse of FIG. 1 after treatment with a 5% alcoholic solution of di(ethyl salicylate) azelate.

The effect of the compounds of the present invention on immunologically-related dermatoses was surprisingly discovered during an attempt to use di(ethyl salicylate) azelate to treat horses which were afflicted by culicoides hypersensitivity. Prior to treatment, the horses had typical occurrence of the disease, including localized dermatitis affecting the mane and poll and the root of the tail. FIG. 1 is a photograph of the mane area of a horse afflicted by culicoides hypersensitivity. The area is irritated and shows significant hair loss. The skin at the affected areas looked hairless, ridged and scaly. The shoulder area and hind quarters were also affected. The horses were treated topically with a 5% alcoholic solution of di(ethyl salicylate) azelate, twice daily for two weeks. After one week of treatment, there was a marked improvement in the appearance of all treated lesions. Hair regrew and the skin looked healthy, as is shown in FIG. 2.

Bearing in mind the nature of this animal disease and the fact that many human diseases result from allergic and inflammatory-related factors and involve skin manifestation which have similarities to this animal disease, it is expected that the compound of the present invention can treat animal as well as human skin disorders, including atopic and allergic dermatitis. The occurrence of hair growth in an animal model indicates that the compound of the present invention can treat hair loss disorders, including androgenic alopecia, alopecia areata, alopecia universalis and alopecia totalis.

The novel compound of the invention may be prepared according to methods known in the art. Ester synthesis from carboxylic acids and their derivatives is well known to those with ordinary skill in the art. A carboxylic acid and an alcohol may be combined in the presence of an acid catalyst to obtain the desired ester and water. The acyl halide derivative, or other suitable derivative (e.g. tosyl, mesityl, etc.) of the carboxylic acid will also effectively produce the desired ester. For a review of ester synthesis, the reader is directed to Vollhardt, *Organic Chemistry*, Chapter 17.

The following examples are illustrative of the present invention, without constituting any limitations thereon.

EXAMPLE 1

Synthesis of Nonanedioic acid, di-[(2'-ethoxycarbonyl)phenyl]ester (also termed herein "di(ethyl salicylate) azelate"). 80 mmole ethyl salicylate is dissolved in 50 ml pyridine in a three neck flask equipped with a nitrogen inlet and outlet. The solution is cooled to 0° C. Azelaoyl chloride (40 mmole) is added dropwise over 1 hour with magnetic stirring. The reaction mixture is stirred for 2 hours at room temperature and then poured into 200 ml 5% HCl. The mixture is extracted 3 times with methylene chloride and the organic phase is worked up with sodium bicarbonate and water, and evaporated to give a viscous off-white product. The product is purified on a silica gel column using 3:5 ethyl acetate:hexane as an eluent. It is then evaporated and mixed overnight with 50 ml hexane to give 11.6 grams (24 mmole; 60% yield) white powder (mp=34–35 C.; MW=485). The compound was characterized by NMR and IR. NMR: 1.25–2.04, m, 10H; 2.63, t, 4H; 4.32, dd, 4H; 7.08, d, 2H; 7.30, t, 2H; 7.52, t, 2H; 7.99, d, 2H; and IR: 1769, 1757, 1713, 1606, 1365, 1255, 1198, 1140, 1088, 770, 715. Elemental analysis: C=67.25 (calc. 66.94); H=6.68 (calc. 6.61).

EXAMPLE 2

Synthesis of o,o-di-(7-methoxycarbonyl-1-octanoyl-1,4-dihydroxybenzene). 20 grams (100 mmole) azelaic acid monoethyl ester is added dropwise over a period of 5 hours into 24 grams (14.7 mmole) $SOCl_2$ over a 40–50 C. water bath. The $SOCl_2$ was distilled out, and the resulting acyl chloride was slowly dropped into 12 grams (110 mmole) hydroquinone at room temperature with magnetic stirring. The reaction mixture was further stirred at room temperature for 16 hours, then poured into 5% HCl. It was extracted with methylene chloride, washed with water, dried and evaporated. Crystallization from toluene gave 17 grams (58 mmole; yield=58%) pale-brown solid (mp=53–56° C.). The compound was characterized by NMR. NMR: 1.31–1.77, m, 20H; 2.3, t, 4H; 2.54, t, 4H; 3.67, s, 6H; 7.07, s, 4H.

EXAMPLE 3

Synthesis of o-(7-methoxycarbonyl-1-octanoyl-1,4-dihydroxybenzene). 20 grams (100 mmole) azelaic acid monomethyl ester is added dropwise over the course of 5 hours into 24 grams (14.7 mmole) $SOCl_2$ over a 40–50 ° C. water bath. $SOCl_2$ was distilled out, and the resulting acyl chloride was slowly dropped into 5.5 grams (50 mmole) hydroquinone at room temperature with magnetic stirring. The reaction mixture was further stirred at room temperature for 16 hours, then poured into 5% HCl. It was extracted with methylene chloride, washed with water, dried, evaporated and mixed overnight with 50 ml hexane, to give 9.5 grams (20 mmole; yield=40%) white powder. The compound was characterized by NMR and IR. NMR: 1.31–1.77, m, 10H; 2.32, t, 2H; 2.53, t, 2H; 3.67, s, 3H; 5.60, broad s, 1H; 6.82, dd, 4H; and IR: 3458,2943, 1740, 1510, 1444, 1267, 1223, 1149.

EXAMPLE 4

Synthesis of di-retinyl azelate. Vitamin A (retinol, 0.86 g, 3 mmole) was dissolved in 2 ml pyridine and 7.5 ml methylene chloride in a 25 ml flask equipped with a calcium chloride vent. The solution was cooled over an ice bath. Azelaoyl chloride (0.3 ml, 0.345 g, 1.5 mmole) was added with magnetic stirring. The reaction mixture was stirred for 2 hours at room temperature and then poured into 10 ml 5% HCl/ice. The mixture was extracted 3 times with methylene chloride and the organic phase is washed with sodium bicarbonate and water, dried with magnesium sulfate and evaporated. The product was purified on a silica gel column, to yield 0.5 gr. (0.7 mmole, yield=46%). The compound was characterized by NMR: 1.0, s, 12H; 1.3–1.6, m, 18H; 1.70, s, 6H; 1.88, s, 6H; 1.95, s, 6H; 2.0, t, 4H; 2.30, t, 4H; 4.72, d, 4H; 5.6, t, 2H, 6.0–6.2, m, 6H; 6.27, d, 2H; 6.63, t, 2H.

EXAMPLE 5

Preparation of an antiacne/antiseborrheic lotion. 10 grams of di(ethyl salicylate)azelate is dissolved in 10 ml ethanol and 90 ml PEG400 to give a clear, colorless solution with viscosity <100cps.

EXAMPLE 6

Efficacy of di(ethyl salicylate)azelate (10%) in the rabbit ear acne model. Three mature male albino rabbits were treated as follows. The external ear canals on both ears were treated once daily for five weekdays for three weeks with 1% crude coal tar in Hydrophilic Ointment USP. Then one ear was treated with antiacne lotion of Example 4 once daily for five weekdays for three weeks while the opposite ear served as an untreated control. Excision biopsies were taken from both sides at the end of three weeks of treatment. These were fixed in foimalin, semi-serial sectioned and stained with H and E. The untreated ears showed compact hyperkeratosis of the sebaceous ducts. These were judged to be moderate examples of comedones with distortion of the follicular infundibulum by dense horn. All three treated ears showed a marked reduction of the comedones. A few follicles showed a small amount of residual horn but this was loose and not compact. The comedolytic effect of di(ethyl salicylate)azelate was comparable to the effect of 0.025% Retin A Cream. There was no inflammatory reaction resulting from the treatment.

EXAMPLE 7

Human skin irritation test. The following lotions (0.1 ml) were applied to the skin of a human subject for 48 hours, using standard skin irritation test chambers (0.64 sq. cm.):

(1) 20% di(ethyl salicylate)azelate (400 mmole/ml), dissolved in PEG-400/ethanol 1:1;

(2) mixture of 7.5% azelaic acid (400 mmole/ml) and 11% salicylic acid (800 mmole/ml), dissolved in PEG-400/ethanol 1:1; and (3) PEG-400/ethanol 1:1 (placebo).

Upon removal of the chambers and 1, 24 and 48 hours later, there was no sign of any skin reaction resulting from the application of either the placebo or di(ethyl salicylate) azelate. The equimolar mixture of the prodrug-components (2) induced an inflammatory response including moderate erythema, slight edema, and local pruritus.

EXAMPLE 8

Acute dermal toxicity/irritation test. The purpose of this study was to evaluate the acute potential dermal irritation effect on skin following the topical application of di(ethyl salicylate) azelate, in rabbits. This test is a modified version of the original Draise method, as described in OECD guidelines. 0.5 ml of either di(ethyl salicylate)azelate (10% or 20%, dissolved in PEG-400/ethanol 1:1) or the vehicle alone were applied to the skin of three rabbits for 24 hours. Rabbits were examined for signs of skin irritation 1, 24 and 72 hours after the removal of the test solutions. Throughout the study, no signs of skin irritation were observed. Based on the current protocol it was concluded that di(ethyl salicylate) azelate is a non-irritant agent.

EXAMPLE 9

Acute subcutaneous toxicity limit test. Five male and five female ICR mice were administered subcutaneously 2000 mg/kg of di(ethyl salicylate) azelate, then followed up for fourteen days. No toxic effects were observed throughout the treatment and observation period, indicating that di(ethyl salicylate) azelate may be regarded as non-toxic.

EXAMPLE 10

Sebolytic effect of di(ethyl salicylate)azelate. The antiacne/antiseborrheic lotion of Example 5 was topically applied twice daily to the forehead of a woman who had oily skin prior to treatment. Skin oiliness was tested using "Skin Tester, Model STC20" (IMS Ltd., Haifa, Israel) prior to treatment and 14 days thereafter. Prior to treatment, the sebum value was 223 units, typical of oily skin. The sebum value after two weeks of treatment was 205 units, corresponding to normal skin.

EXAMPLE 11

Antipsoriatic gel. 20 g di(ethyl salicylate)azelate is dissolved in 50 ml ethanol and 50 ml water. The solution is warmed to 60 C. with stirring and 1 g PEG-4000 is added. The mixture is cooled to room temperature and a gentle magnetic stirring is applied for 2 hours.

EXAMPLE 12

Modulation of keratinocyte proliferation. The effect of di(ethyl salycilate)azelate and di-retinyl azelate on cell proliferation and cell viability was tested in vitro using human keratinocyte culture system.

Cell proliferation assay.

50,000 human keratinocytes from secondary culture were seeded into 24 well plates, in 1 ml DMEM-F12 medium (Green H. (1978) Cell 15:801–805) with growth factors and 10% Fetal Calf Serum. The cells were incubated at 37° C. in 5% $CO_2$ until 30–40% confluency was reached and then the various test materials, dissolved in ethanol, were added in volumes of 0.1–20 μl, to final volume of 0.5 ml. The same volumes of ethanol were added to control cultures, for comparative values of ethanol cytotoxicity. No apparent cytotoxicity was found up to 40 μl ml ethanol. The medium was replaced with fresh medium prior to addition of the test materials. The cultures were further incubated for 3 days at 37° C. and 5% $CO_2$ and then washed with phosphate buffered saline (PBS). Cell numbers were determined using two methods: 1) trypsinization, followed by cell counting; and 2) fixation of the culture with p-formaldehyde 2% in PBS and methylene blue staining, followed by extraction of color and optical density measurement at 650 nm. Both methods were found in good correlation, so that 1 OD unit corresponded to 1,000,000 cells. IC50, i.e., the concentration that caused 50% inhibition of cell proliferation for each of the test materials is presented in Table 1.

Cytotoxicity test.

Keratinocyte cells, as above, were allowed to proliferate in medium, without the test materials, up to 100% confluency, with one exchange of medium during growth. Confluent cultures were incubated with increasing concentrations of the test materials in ethanol for three days at 37° C. and 5% $CO_2$. At the end of the incubation period the cultures were washed with PBS and measured for remaining attached cells using the above described methods. LC50, i.e., the concentration that caused 50% cytotoxicity is also presented in Table 1.

Table 1 demonstrates that di-retinyl azelate and di(ethyl salicylate) azelate are significantly more potent than azelaic acid and salicylic acid in inhibiting cell proliferation. Moreover, their cytotoxic concentrations were 6.6–10 fold higher than their inhibitory concentrations, rendering them safer than free azelaic acid.

TABLE 1

IC50 (inhibitory concentration) and LC50 (cytotoxic concentration) of compounds of the invention, azelaic acid and salicylic acid

| Test Material | IC50 | LC50 | Safety factor (CD50/ID50) |
|---|---|---|---|
| Di-retinyl azelate | 15 μM | 100 μM | 6.6 |
| Di(ethyl salicylate) azelate | 0.3 mM | 3 mM | 10 |
| Azelaic acid | 1.5 mM | 4 mM | 2.6 |
| Salicylic acid | 1.6 mM | 6 mM | 3.8 |

EXAMPLE 13

This example demonstrate the effectiveness of di(ethyl salicylate)azelate in the treatment of allergic dermatoses.

The effect of di(ethyl salicylate) azelate on culicoides hypersensitivity was tested in two horses with colicoides hypersensitivity. Prior to treatment, both horses had typical occurrence of the disease, including localized dermatitis affecting the mane and poll and the root of the tail. The shoulder area and hind quarters were also affected. The skin at the affected areas looked hairless, ridged and scaly. The horses were treated topically with a 5% alcoholic solution of di(ethyl salicylate)azelate, twice daily for two weeks. After one week of treatment, there was a marked improvement in the appearance of all treated lesions (see photographs at baseline and on Day 5, FIGS. 1 and 2, respectively). As clearly seen in the pictures, hair seemed to regrow and the skin looked healthy. This improvement persisted throughout 14 days of treatment and observation.

EXAMPLE 14

Anti-acne and anti-inflammatory effect of di(ethyl salicylate) azelate. Four cats were admitted to the veterinary clinic with skin lesions identified as chin acne. One additional cat had localized furunculosis (eczema) on the chin. The area of the skin lesions was 1–4 cm² at baseline. All animals were previously treated with either benzoyl peroxide or topical steroids with no response. Cats were treated twice daily for 14 days with a 5% alcoholic solution of di(ethyl salicylate) azelate. Three of the four cats responded to treatment within 10 days, with the skin lesions deisappearing and the bald areas exhibiting new hair growth. The furunculosis-afflicted cat also responded positively to the same treatment. No skin irritation was noticed in any of the treated cats.

What is claimed is:

1. A method of treating dermatological disorders, comprising:

administering topically, nasally, orally or parenterally to a subject having said dermatological disorder a therapeutically effective amount of a compound comprising a mono- or diester of an α,ω-dicarboxylic acid, wherein at least one ester moiety of the said compound comprises a keratolytically active alcohol.

2. The method of claim 1, wherein the compound has the formula,

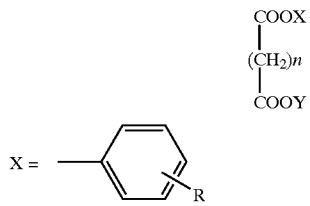

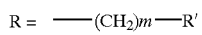

where n is in the range of 4 to 12; m is in the range of 0 to 8; R' is selected from the group consisting of H, alkyl, aryl, alkenyl, benzyl, OH, NHR", CONHR" and COOR"; R" is selected from the group consisting of alkyl, aryl, alkenyl, and benzyl; and Y is selected from the group consisting of H, alkyl, aryl, alkenyl, benzyl and X.

3. The method of claim 1, wherein said compound is applied topically to an affected area.

4. The method of claim 1, wherein said dermatological disorder is linked to hyperkeratinization, hypertrophy of the stratum corneum, excess sebum secretion, microbial infection, dermatophytoses, or increased conversion of testosterone to dihydrotestosterone.

5. The method of claim 1, wherein said dermatological disorder is selected from a group consisting of acne, seborrheic dermatitis, dandruff, psoriasis, ichthyosis, Rosacea, hirsutism, hypertrichosis, and androgenic alopecia.

6. The method of claim 1, wherein said dermatological disorder comprises hair growth disorders selected from the group consisting of alopecia areata, alopecia universalis and alopecia totalis.

7. The method of claim 1, wherein said dermatological disorder comprises excessive body hair growth.

8. The method of claim 1, wherein said dermatological disorder comprises of allergic dermatoses.

9. The method of claim 1, wherein said dermatological disorder comprises veterinary inflammatory and allergic skin disorders.

10. The method of claim 1, wherein said dermatological disorder comprises insect bite allergy.

11. The method of claim 1 wherein said subject is human or animal.

12. The method of claim 2, wherein said compound is a liquid at 40° C.

13. The method of claim 2, wherein n is in the range of 6 to 10.

14. The method of claim 2, wherein said α,ω-dicarboxylic acid comprises azelaic acid.

15. The method of claim 2, wherein the α,ω-dicarboxylic acid carbon chain backbone is unsaturated.

16. The method of claim 15, wherein the backbone comprises about one to three double bonds.

17. The method of claim 2, wherein the α,ω-dicarboxylic acid moiety is linked to a hydrocarbon substituent.

18. The method of claim 2, wherein the α,ω-dicarboxylic acid moiety is substituted by alkyl, aryl, alkenyl or benzyl groups.

19. The method of claim 2, wherein said keratolytic alcohol is selected from a group consisting of ortho-, meta- and para-hydroxyalkylbenzoate, ortho-, meta-, and para-dihydroxybenzene, ortho-, meta-, and para-hydroxytoluene and derivatives thereof.

20. The method of claim 2, wherein said keratolytically active alcohol comprises an ortho-, meta- and para-hydroxyalkylbenzoate.

21. The method of claim 1, wherein the keratolytically active alcohol moiety comprises a retinol moiety or derivatives thereof.

22. The method of claim 1, wherein the keratolytically active alcohol moiety comprises an α-hydroxy acid moiety or derivatives thereof.

23. A method of increasing penetration of an α,ω-dicarboxylic acid across the skin, comprising:

applying a mono or diester of the α,ω-dicarboxylic acid to the skin, said ester moiety comprises a keratolytically active alcohol moiety.

24. A method of increasing penetration of a salicylic acid across the skin, comprising:

applying a mono or disalicylate ester derivative of the α,ω-dicarboxylic acid to the skin.

25. A compound, comprising:

an α,ω-dicarboxylic acid covalently linked through an ester bond with at least one keratolytically active alcohol moiety, having the formula,

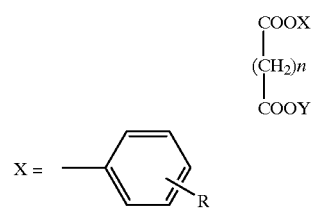

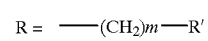

where n is in the range of 6 to 12; m is in the range of 0 to 8; R' is selected from the group consisting of aryl, alkenyl, benzyl, OH, NHR", CONHR" and COOR"; R"

is selected from the group consisting of alkyl, aryl, alkenyl, and benzyl; and Y is selected from the group consisting of H, alkyl, aryl, alkenyl, benzyl and X.

26. The compound of claim 25, characterized in that the compound is a liquid at 40° C.

27. The compound of claim 25 wherein n is in the range of 6 to 9.

28. The compound of claim 25 wherein the α,ω-dicarboxylic acid carbon chain backbone is unsaturated.

29. The compound of claim 28, wherein the backbone comprises about one to three double bonds.

30. The compound of claim 25 wherein the carbon chain of the α,ω-dicarboxylic acid moiety is linked to a hydrocarbon substituent.

31. The compound of claim 25 wherein the carbon chain of the α,ω-dicarboxylic acid moiety is substituted by alkyl, aryl, alkenyl or benzyl groups.

32. The compound of claim 25 wherein said α,ω-dicarboxylic acid comprises azelaic acid.

33. The compound of claim 25 wherein said keratolytically active alcohol comprises an ester, anhydride or amide derivative of salicylic acid or a derivative thereof.

34. A pharmaceutical or cosmetic composition, comprising:

a therapeutically effective amount of a compound comprising a mono- or diester of an α,ω-dicarboxylic acid, wherein the ester comprises a keratolytically active alcohol moiety, and having the formula $$\begin{array}{c} COOX \\ | \\ (CH_2)n \\ | \\ COOY \end{array}$$

X = 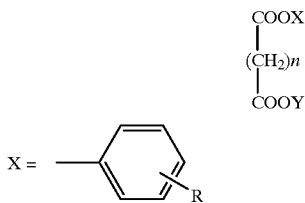

R = ———(CH$_2$)$m$———R' where n is in the range of 6 to 12; m is in the range of 0 to 8; R' is selected from the group consisting of H, alkyl, aryl, alkenyl, benzyl, OH, NHR", CONHR" and COOR"; R" is selected from the group consisting of alkyl, aryl, alkenyl, and benzyl; and Y is selected from the group consisting of H, alkyl, aryl, alkenyl, benzyl and X; and a pharmaceutically or cosmetically acceptable carrier.

35. The pharmaceutical or cosmetic composition of claim 34 wherein the α,ω-dicarboxylic acid comprises azelaic acid.

36. The pharmaceutical or cosmetic composition of claim 34 wherein the compound is a liquid at 40° C.

37. The pharmaceutical or cosmetic composition of claim 34 wherein the α,ω-dicarboxylic acid carbon chain backbone is unsaturated.

38. The pharmaceutical or cosmetic composition of claim 34 wherein the backbone comprises about one to three double bonds.

39. The pharmaceutical or cosmetic composition of claim 34 wherein the α,ω-dicarboxylic acid moiety is linked to a hydrocarbon substituent.

40. The pharmaceutical or cosmetic composition of claim 34 wherein the α,ω-dicarboxylic acid moiety is substituted by alkyl, aryl, alkenyl or benzyl groups.

41. The pharmaceutical or cosmetic composition of claim 34 wherein said keratolytic alcohol is selected from a group consisting of ortho-, meta- and para-hydroxyalkylbenzoate, ortho-, meta-, and para-dihydroxybenzene, ortho-, meta-, and para-hydroxytoluene and derivatives thereof.

42. The pharmaceutical or cosmetic composition of claim 34 wherein said keratolytically active alcohol comprises an ortho-, meta- and para-hydroxyalkylbenzoate.

43. A pharmaceutical or cosmetic composition comprising:

a therapeutically effective amount of a compound comprising a mono- or diester of an α,ω-dicarboxylic acid with a keratolytically active alcohol, wherein the keratoyltically active alcohol comprises an α-hydroxy acid or derivatives thereof; and a pharmaceutically or cosmetically acceptable carrier.

44. A pharmaceutical or cosmetic composition comprising:

a therapeutically effective amount of a compound comprising a mono- or diester of an α,ω-dicarboxylic acid of a keratolytically active alcohol, wherein the keratolytically active alcohol comprises a retinol moiety or derivatives thereof; and a pharmaceutically or cosmetically acceptable carrier.

45. The pharmaceutical or cosmetic composition of claim 34, 43, or 44 wherein said therapeutically effective amount comprises and amount effective to treat a skin disorder.

46. The pharmaceutical or cosmetic composition of claim 34, 43, or 44 wherein said therapeutically effective amount of said compound comprises an amount effective to treat dermatological disorders selected from the group consisting of hyperkeratinization, hypertrophy of the stratum corneum, excess sebum secretion, microbial infection, dermatophytoses, or increased conversion of testosterone to dihydrotestosterone.

47. The compound of claim 25, where said compound is functional to release a plurality of dermatologically-active compounds when delivered to a target site of the skin.

48. The compositions of claim 34, wherein said composition is functional to release a plurality of dermatologically-active compounds when delivered to a target site of the skin.

* * * * *